United States Patent [19]

Utterberg et al.

[11] Patent Number: 5,704,924
[45] Date of Patent: Jan. 6, 1998

[54] EASY USE NEEDLE PROTECTOR SHEATH

[75] Inventors: David S. Utterberg, Seattle, Wash.;
William J. Schnell, Libertyville, Ill.

[73] Assignee: Medisystems Technology Corporation, Seattle, Wash.

[21] Appl. No.: 584,451

[22] Filed: Jan. 11, 1996

[51] Int. Cl.[6] ............................................ A61M 5/00
[52] U.S. Cl. ...................... 604/263; 604/162; 604/171; 604/198
[58] Field of Search ........................... 604/162, 163, 604/171, 174, 177, 192, 197-9, 110, 263; 128/912, 919, DIG. 26

[56] References Cited

U.S. PATENT DOCUMENTS

| | | |
|---|---|---|
| 4,917,669 | 4/1990 | Bonaldo . |
| 4,935,011 | 6/1990 | Hogan ................................. 604/162 |
| 4,941,881 | 7/1990 | Masters et al. . |
| 4,946,447 | 8/1990 | Hardcastle et al. . |
| 4,994,046 | 2/1991 | Wesson et al. . |
| 5,092,461 | 3/1992 | Adam ................................... 604/263 |
| 5,112,311 | 5/1992 | Utterberg et al. . |
| 5,120,320 | 6/1992 | Fayngold . |
| 5,171,231 | 12/1992 | Heiliger ............................... 604/192 |
| 5,219,339 | 6/1993 | Saito . |
| 5,266,072 | 11/1993 | Utterberg et al. ................... 604/192 |
| 5,290,264 | 3/1994 | Utterberg . |
| 5,330,438 | 7/1994 | Gollobin et al. . |
| 5,350,368 | 9/1994 | Shields ................................. 604/177 |
| 5,425,720 | 6/1995 | Rogalsky et al. ................... 604/198 |
| 5,562,636 | 10/1996 | Utterberg ............................. 604/177 |
| 5,562,637 | 10/1996 | Utterberg ............................. 604/177 |

FOREIGN PATENT DOCUMENTS

| | | |
|---|---|---|
| 0 265 159 A2 | 4/1988 | European Pat. Off. . |
| 0 265 159 A3 | 4/1988 | European Pat. Off. . |
| 0 353 916 | 2/1990 | European Pat. Off. . |
| 0 459 953 A1 | 12/1991 | European Pat. Off. . |
| 1-212561 | 2/1988 | Japan . |
| WO 95/24232 | 9/1995 | WIPO . |

Primary Examiner—Michael Buiz
Assistant Examiner—Bhisma Mehta
Attorney, Agent, or Firm—Gerstman, Ellis & McMillin, Ltd.

[57] ABSTRACT

A medical needle protector sheath which comprises a body having a top wall, side walls, an open first end, and slot formed in each side wall to receive a needle wing extending through each of the slots. The slots extend from the first end toward a second sheath end opposed to the first end, with the slots terminating in the side walls at end points which are spaced from the second end. Typically, first portions of the slots adjacent to the end points slope away from the top wall as the slots extend toward the second end. Other portions of the slots slope toward the top wall as the slots extend to the second end. Various improvements are described which result in safer-and easier use of the needle protector sheath.

21 Claims, 1 Drawing Sheet

U.S. Patent  Jan. 6, 1998  5,704,924
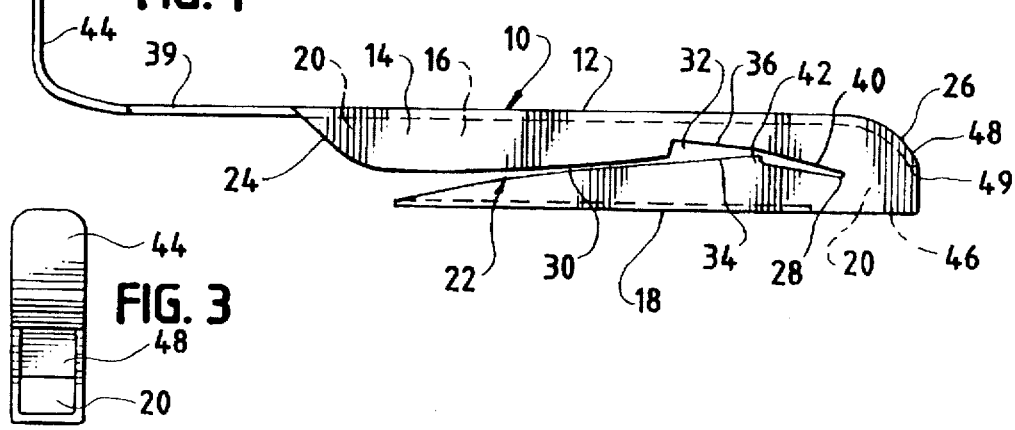
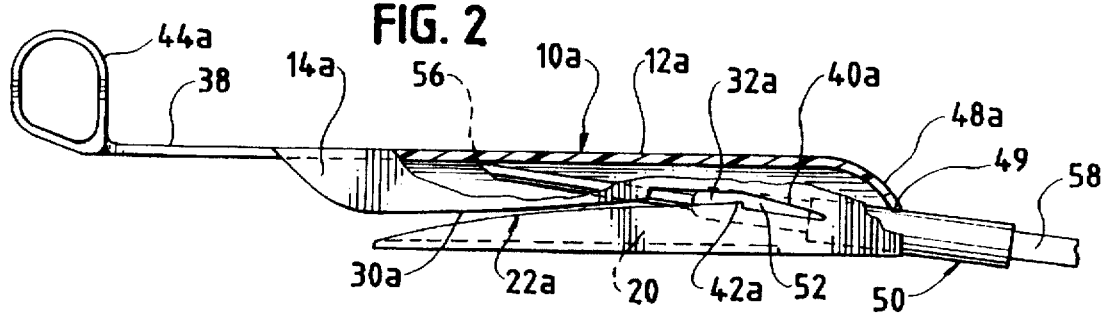
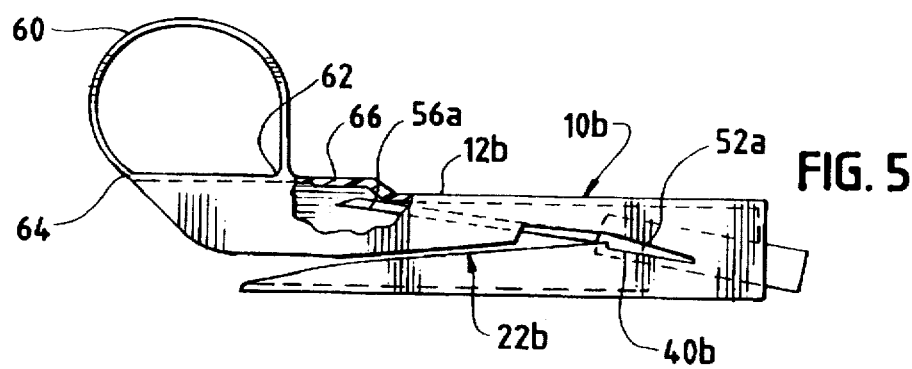
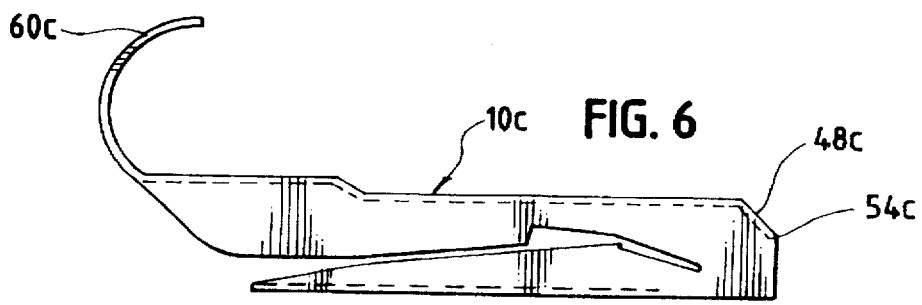

EASY USE NEEDLE PROTECTOR SHEATH

BACKGROUND OF THE INVENTION

Many types of needle protector sheaths are known. Particularly, needle protector sheaths for winged needles are presently in clinical use, in which the wings of the needle project outwardly through slits defined in the sheath, so that the sheath can slide from a retracted position while the needle is in use to an advanced positioned in which the needle is enclosed, the sheath being locked in that position so that the point of the needle is recessed in the sheath and cannot cause accidental injury. For examples of such devices, see Utterberg et al U.S. Pat. No. 5,112,311; Shields U.S. Pat. No. 5,350,368; Gollobin et al. U.S. Pat. No. 5,330,438; Masters et al. U.S. Pat. No. 4,941,881; Japanese Patent Publication 1-212,561; and Fayngold U.S. Pat. No. 5,120,320 among others.

As one disadvantage of such protector sheaths for needles, since they carry a slit it is at least remotely possible for the needle to rotate in a horizontal manner after it has been placed in the sheath, causing the needle tip to project laterally out of one of the slits, where it may cause accidental injury.

As another issue, the clinicians who use the needle protector sheaths wish to make sure that the wings of the needles are securely latched into a rear end portion of the slots as the sheath is advanced, so that the sheath will not accidentally retract, again exposing the needle. With earlier designs, some difficulties have been encountered in easily moving the needle and wings into a retracted, latched position where the needle tip is securely recessed, while at the same time assuring that the point of the needle is securely retained within the sheath in a position where it cannot shift and project laterally outwardly through one of the slots.

By this invention, improvements are provided to medical needle protector sheaths to give greater assurance that the sheath and needle are locked together after needle use, with the needle being reliably positioned in retracted position within the sheath, so that any possible accidental failure resulting in the needle projecting out of the sheath again is eliminated.

DESCRIPTION OF THE INVENTION

By this invention, a medical needle protector sheath comprises a body having a top wall, side walls, an open first end, and a slot formed in each side wall to receive a needle wing extending through each of the slots. The slots extend from the first end toward a second end opposed to the first end, with the slots terminating in the side walls at end points which are spaced from the second end.

First portions of the slots are positioned adjacent to the end points, the first slot portions sloping away from the top wall as the slots extend toward the second end.

The protector sheath further preferably comprises a bottom wall which is connected to the side walls. The bottom wall is spaced inwardly from the second end of the sheath to define a recess. This can permit a needle and hub positioned in the sheath, particularly with the needle wings positioned in the first, sloping slot portions, to be tilted so that the needle tip engages and can dig into the top wall. As this takes place, the hub may occupy at least some of the recess defined by the inward spacing of the bottom wall.

It is also preferred for an end wall to be defined at the second end of the sheath. This end wall extends from the vicinity of the top wall, and is preferably integral therewith. The end wall may define a smooth, downwardly extending curve from the top wall, or may be of another shape, extending downwardly to a position above the bottom wall to provide room for the needle hub and connected tubing to extend out of the second end of the sheath. The end wall firmly holds and constrains the needle and hub in a desired acute angle to the top wall, which acute angle may correspond to a lesser or equal angle of the first portions of the slots. Typically, the needle hub or tubing may abut the lower edge of the end wall, which prevents it from being raised or rotated to put the needle and hub into a more parallel relation with the protector sheath. At the same time, the needle and hub may constrained against rotation in the other direction by the impinging of the needle tip against the top wall of the sheath. Thus, the needle and hub may not only be retained in firm, non-moving relation to the sheath by conventional first catch projections defined in the first portions of the slots, but it can be held against rotation relative to the sheath by the points of impingement at the bottom of the end wall and between the needle point and the top wall.

It is also preferred for the slots to define second portions, which are positioned adjacent to the first slot portions but nearer to the first end than the first slot portions. These optional second slot portions define a greater slot width than other slot portions, to permit a degree of free vertical rotation of the wings of a medical needle which occupy the second slot portion. Thus, while the needle occupies the second slot portion, it can rotate with ease through a certain, constrained angle. This is particularly advantageous when, as is preferred, most of the parts of the slots positioned between the first slot portion and the first sheath end slope toward the top wall as the slots extend towards the second end. Such a slot shape without the second portions is taught in the co-pending Utterberg U.S. application Ser. No. 08/420,700, filed Apr. 11, 1995, now U.S. Pat. No. 5,562,637 and Utterberg application Ser. No. 08/275,880 filed Jul. 15, 1994, now U.S. Pat. No. 5,562,636. Since the respective slots first extend upwardly toward the top wall, and then curve downwardly again away from the top wall, the needle and hub must rotate as their wings slide along the slots, when the needle is being retracted into the sheath. The second portions of the slots, permitting a degree of free rotation of the needle, facilitate the retraction process, reducing the force necessary to bring the sheath and needle together into latched relationship.

It is also preferred for an upstanding handle for manual retention of the sheath to project from the top wall at or near the first end of the sheath. This provides a better grip on the sheath than has been previously provided, so that the needle may be pulled from its position within the patient by pulling the connected tube, causing the needle to retract to slide along the slots, and to latch into position with a discernable snap. This indicates reliable latching of the sheath in protective position around the needle. While one finger holds the upstanding handle, other fingers of the user may press overlying gauze (as generally described in the previously cited Utterberg U.S. Pat. No. 5,112,311) to suppress bleeding after needle removal in conventional manner.

If desired, the upstanding handle may be a finger ring. The handle may be defined on a forward extension of the top wall which extends forwardly beyond the side walls at the first end.

It also may be desirable for the top wall of the sheath to define an elevated portion adjacent to the first end, which correspondingly provides an elevated space inside the sheath. This permits use of the sheath with longer needles, providing a broader range of needle lengths with which a single protector sheath may be used.

By the use of the above features either together in various combinations or separately, significant advantages may be achieved in the use and handling of winged needle protector sheaths.

DESCRIPTION OF THE DRAWINGS

In the drawings,

FIG. 1 is an elevational view of a first embodiment of the needle sheath of this invention.

FIG. 2 is an elevational view of a second embodiment of the needle sheath of this invention, showing a needle carried therein.

FIG. 3 is an end elevational view of the needle sheath of FIG. 1 and FIG. 2.

FIG. 4 is a bottom plan view of the needle sheath of FIG. 1 and FIG. 2.

FIG. 5 is a side elevational view of a third embodiment of the needle sheath of this invention.

FIG. 6 is a side elevational view of a fourth embodiment of the needle sheath of this invention.

DESCRIPTION OF SPECIFIC EMBODIMENTS

Referring to the drawings, FIG. 1 shows a hollow needle sheath 10 which has a top wall 12, side walls 14, 16, and a bottom wall 18, being positioned in rectangular array in a manner similar to that shown in FIG. 3. Needle sheath 10 also defines an inner bore or lumen 20 of generally rectangular shape, being at least partially open at each end.

Sheath 10 also defines slots 22 extending through first end 24 of the sheath and extending toward second end 26. Each of slots 22 are of substantially identical shape and terminate at respective end points 28 at a position spaced from second end 26.

As shown in FIG. 2, sheath 10 may be threaded on a winged needle which is connected to a tube in conventional manner. The needle may be originally positioned in the venous system of a patient. Thus, when the needle is withdrawn, it slides to the rear, with the wings entering slots 22 or 22a. Initially the needle is angled slightly upwardly as it occupies the skin of the patient, similar to that shown in FIG. 14 of Utterberg Pat. No. 5,112,311, at an angle approximately parallel to the forward section 30 of slot 22 as it rests on the skin of the patient. Thus, as the needle is pulled backwards out of the patient, it slides diagonally upwardly along forward slot sections 30, 30a in a manner that minimizes twisting and bending of the needle while the needle tip remains in the patient.

Then, the wings of the needle enter a second slot section 32, 32a as defined above, which is of increased width relative to other portions of the slots 22. Because of this increased width, the needle wings are free to rotate out of connection, for example, with the lower edge 34 of slot connection 32 into engagement with upper edge 36 of second slot section 32, causing the needle to rotate in clockwise manner into a position similar to that shown in FIG. 2. FIG. 2 shows a needle sheath similar in its basic construction to that of FIG. 1 except for the construction of upstanding handle 44, 44a, carried on a forward extension 39, 38 of upper wall 12, 12a.

The needle is pulled backwards into snap-fit relation with a first section 40, 40a of the slots, which section carries a generally conventional catch projection 42, 42a for retention of the wings in the respective first slot sections 40, 40a. The presence of the widened second slot section 32, 32a permits the spontaneous rotation and the easy transition of the needle and wings to a different angle as the needle is drawn backwards into sheath 10 and into locking relation therewith in first slot section 40. Thus, the necessary pulling force to accomplish this is reduced.

Upstanding handle 44 of FIG. 1 simply represents an upwardly turned projection which may be retained by the finger of the user's hand. Typically with the same hand, the user is covering the needle injection site of the patient with gauze pads. Thus, one can remove the needle from the patient by pulling the hub or its connected tubing 58, causing the needle to retract into the sheath. As this is done, one can firmly hold handle 44, 44a of the sheath with one finger to prevent it from retreating with the needle.

In FIG. 2, the upstanding handle 44a may be a hollow tube or a ring, preferably of approximately the width of sheath 10a as shown in FIG. 4. The various reference numerals of FIGS. 2 and 4 which end with suffix "a" correspond to the parts referred above by the corresponding numbers of FIGS. 1 and 3 without the suffix. For example, bottom wall 18a of FIGS. 2 and 4 correspond to bottom wall 18 of the FIG. 1 embodiment.

Both of the embodiments of FIGS. 1 and 2 define a bottom wall 18, 18a which are connected to the side walls, but are spaced inwardly from the second end 26, 26a to form an optional recess 46, 46a. Coupled with this, it is preferred for an end wall 48, 48a to connect with the top wall 12, 12a and to curve downwardly from the top wall to a bottom position 49 above bottom wall 18, 18a that permits winged needle and hub assembly 50 to extend into the bore 20 underneath end walls 48, 48a. Typically, as shown in FIG. 2, the wings 52 of assembly 50 are held in an angle to the longitudinal axis of sheath 10, 10a as they occupy first portion 40, 40a of the slots, which first portion occupies a similar angle. The presence of end wall 48 prevents assembly 50 from rotating upwardly by flexing wings 52, because such counterclockwise rotational motion is prevented by the abutment of assembly 50 against the lower edge of end wall 48 or 48a. However, needle and hub 50 does not have to abut end wall 48. It may be spaced from it.

Also, in the fully retracted, locked configuration of needle assembly 50 as shown in FIG. 2, the upwardly angled needle point 56 preferably presses against top wall 12a, being directed there by the angle and position of slot portions 40a and the position of the lower edge of end wall 48a. Thus, needle tip 56 presses against top wall 12, 12a when in its fully retracted and locked position, with the wings being locked in generally conventional manner in first slot portion 40a. This also prevents needle assembly 50 from rotating in clockwise manner around the flexible wings, so that the needle assembly is rigidly affixed within sheath 10a, being incapable of rotation about the flexible wings 52 because of the engagement at the lower edge of end wall 48 and at the point of engagement of needle tip 56 against the undersurface of top wall 12a.

The aperture 46a in the bottom wall makes is possible for needle assembly 50 to project slightly below the side walls as necessary to achieve this configuration. Also, if desired, the wall that defines aperture 46a may serve as a secondary catch for the annular face of the tubing 58 to which the needle is attached.

Similar relationships may be applied between a winged needle hub and the FIG. 1 embodiment.

Referring to FIG. 5, another embodiment of the sheath of this invention is disclosed. Sheath 10b can be of identical structure to that of the previous designs except as otherwise described herein. The difference lies near the first end of sheath 10b, while slot 22b and most of the length of the respective walls can be identical to the above.

It can be seen that on the left side of the sheath of FIG. 5, the extension of top wall 38, 39 has been eliminated, and a different, upstanding handle 60 is provided in the form of a finger ring which attaches to top wall 12b at two different places 62, 64. Also, top wall 12b defines an externally and internally elevated portion 66, which allows longer needles 56a or shorter needles to be retained in the same guard, with their respective wings 52a sliding along the slot 22b into first slot portion 40b with substantially the same catchment angle as shorter needles. Upstanding finger ring 60 provides good ergonomic characteristics, which isolate the needle withdrawal traction forces that may be resisted by the finger in ring 60 from the needed pressure on the overlying gauze by other fingers, as the needle is being withdrawn from the patient, to provide hemostasis.

Apart from that, sheath 10b can be of identical design, and can work in a manner identical to, the sheaths of the previous embodiments. Note that the needle 56a may be placed into the sheath 18a with a point inverted from the position of needle point 56. Either position is suitable for these sheaths.

Referring to FIG. 6, another embodiment of sheath 10c may be of similar structure and function to the previous sheaths except as otherwise described herein. The end wall 48c at the second end of sheath 10c partly but not completely blocks the bore extending through the hollow sheath 10c, to serve as a structure equivalent to end walls 48, 48a for similar purposes of holding the rotational orientation of a needle and hub 50 captured within the sheath. As one difference, end wall 48c may be an angled straight wall, rather than a curved wall as in the previous embodiments, extending down to bottom position 54c.

At the other end of the sheath 10c, the upstanding handle for manual retention 60c comprises a partial arc attached to the rest of sheath 10c at only one end, as shown. This structure is also suitable for being gripped with one finger to hold sheath 10c in its desired position as the needle is being pulled out of the patient and into retracted relation within the sheath 10c.

Upstanding handle members 60, 60c have widths preferably substantially identical to the widths of sheaths 10b, 10c in a manner similar to that generally indicated in FIG. 3, although other widths may be used if desired.

Thus, a sheath for winged medical needles is provided, in which the needle may be comfortably and reliably pulled from the patient while the sheath is manually retained with a finger, and the wings slip into the respective slots 22, to encourage the needle to withdraw from the patients' skin at a shallow angle which approximates the axis of the needle in the skin. This reduces pain. Then, as the needle wings are being withdrawn through slots 22 and enter into the second slot section 32, the needle can spontaneously rotate through a small angle so that the wings become more parallel to the direction of first slot section 40 which extends at a different angle. The needle is thus rotated upwardly so that its tip can press against the lower surface of the upper wall 12, being held there so that the needle cannot accidentally pass through one of the slots to the exterior.

The above has been offered for illustrative purposes only, and is not to be construed as limiting the scope of the invention of this application, which is as defined in the claims below.

That which is claimed is:

1. A medical needle protector sheath which comprises a body having a top wall, side walls, an open first end, and a slot formed in each side wall to receive a needle wing extending through each of said slots; said slots extending from said first end toward a second sheath end opposed to said first end, said slots terminating in said sidewalls at end points spaced from said second end, first portions of said slots adjacent to said end points sloping away from said top wall as said slots extend toward said second end; said protector sheath further comprising a closed bottom wall connected to said sidewalls, said bottom wall being spaced inwardly from said second end to define a recess at said second end to permit a needle defining a tip and hub positioned in said sheath to be tilted so that the needle tip engages said top wall and the hub occupies at least some of said recess.

2. The protector sheath of claim 1 in which an end wall is defined at said second end, said end wall extending from the vicinity of said top wall downwardly to a position above said bottom wall, whereby said needle and hub may be held in the sheath by abutment of said end wall at an acute angle to said top wall.

3. The protector sheath in claim 2 in which said first slot portions adjacent to said end points define first catch projections to prevent needle wings that occupy said slot portions from easily sliding back toward said first end.

4. The protector sheath of claim 3 in which at least most of the lengths of said slots positioned between said first slot portion and the first end slope toward said top wall as said slots extend toward said second end.

5. The protector sheath of claim 4 in which an outwardly extending handle for manual retention of said sheath projects from said top wall adjacent said first end.

6. The protector sheath of claim 5 in which said handle comprises a finger ring.

7. The protector sheath of claim 4 in which said top wall has a portion which extends forwardly beyond the sidewalls at said first end, and carries an upstanding finger ring.

8. The protector sheath of claim 5 in which said top wall defines an elevated portion adjacent said first end, to permit greater use of the sheath with needles of different lengths.

9. The protector sheath of claim 3 in which second portions of said slots, positioned adjacent to said first portions and nearer to the first end than said first portions, define a greater slot width than other slot portions to permit a degree of free vertical rotation of wings of a medical needle occupying said second slot portions.

10. A medical needle protector sheath which comprises a body having a top wall, a bottom wall, side walls, an open first end, and a slot formed in each side wall to receive a needle and hub having a wing extending through each of said slots;

said slots extending from said first end toward a second end opposed to said first end, said slots terminating in said side walls at end points spaced from said second end, first portions of said slots being adjacent to said second end, said protector sheath also having an end wall defined at said second end, said end wall extending from the vicinity of said top wall downwardly to a position above said bottom wall, whereby a needle and hub may be held in the sheath at an acute angle to said top wall by abutment with said end wall, with the needle of said needle and hub pointing toward said top wall.

11. The protector sheath of claim 10 in which said first slot portions adjacent to said end points define first catch projections to prevent needle wings that occupy said slot portions from easily sliding back towards said first slot end.

12. The protector sheath of claim 11 in which at least most of the lengths of said slots positioned between said first slot portion and the first end slope toward said top wall as said slots extend towards said second end.

13. The protector sheath of claim 12 in which an upstanding handle for manual retention of said sheath projects from said top wall adjacent said first end.

14. The protector sheath of claim 12 in which first portions of said slots adjacent to said end points slope away from said top wall as said slots extend toward said second end.

15. The protector sheath of claim 11 in which second portions of said slots, positioned adjacent to said first portions and nearer to the first end than said first portions, define a greater slot width than other slot portions to permit a degree of free vertical rotation of wings of a medical needle occupying said second slot portion.

16. A medical needle protector sheath which comprises a body having a top wall, side walls, an open first end, and a slot formed in each side wall to receive a needle hub wing extending through each of said slots;

said slots extending from said first end towards a second sheath end opposed to said first end, said slots terminating in said side walls at end points spaced from said second end, first portions of said slots adjacent to said end points sloping away from said top wall as said slots extend towards said second end, at least most of the length of said slots positioned between said first slot portion and the first end each defining a forward slot portion sloping toward said top wall as said slots extend towards said second end;

said slots each defining a second portion, positioned between said forward slot portion and said first portion and nearer to the first end than said first portion, said second portion being angled to said first portion and defining a greater slot width than said first portion to permit a degree of free vertical rotation of wings of a medical needle occupying said second slot portions.

17. The protector sheath of claim 16 which further comprises a bottom wall connected to said side walls, said bottom wall being spaced inwardly from said second end to define a recess to permit a needle having a tip and hub positioned in said sheath to be tilted so that the needle tip engages said top wall.

18. The protector sheath of claim 17 in which an upstanding handle is connected to the sheath at said top wall at or near said first end for manual retention of said sheath.

19. The protector sheath of claim 18 in which said upstanding handle comprises a finger ring.

20. The protector sheath of claim 16 in which an upstanding finger ring projects from said top wall adjacent said first end.

21. The protector sheath of claim 16 having an end wall defined at said second end, said end wall extending from the vicinity of said top wall downwardly to a position above said bottom wall, whereby a needle and hub may be held in the sheath at an acute angle to said top wall by abutment with said end wall, with the needle of said needle and hub pointing to said top wall.

* * * * *